United States Patent [19]

Connolly et al.

[11] Patent Number: 5,008,196

[45] Date of Patent: Apr. 16, 1991

[54] STIMULATION OF ENDOTHELIAL CELL GROWTH

[75] Inventors: Daniel T. Connolly, Manchester; Joseph Feder, University City, both of Mo.

[73] Assignee: Monsanto Company, St. Louis, Mo.

[21] Appl. No.: 87,739

[22] Filed: Aug. 21, 1987

[51] Int. Cl.$^5$ .................. C12N 5/00; A61K 37/00; C07K 7/00

[52] U.S. Cl. .................. 435/240.2; 435/240.21; 435/240.23; 435/240.31; 530/324; 530/380; 514/12; 514/21

[58] Field of Search ........... 435/240.31, 240.25, 435/68, 70, 1, 70.3, 240.3, 802; 424/95; 514/12, 21, 56; 530/324, 380, 829, 399

[56] References Cited

U.S. PATENT DOCUMENTS 4,456,550 6/1984 Dvorak et al. .................. 260/112 R
4,721,672 1/1988 Vallee et al. .................. 435/70

OTHER PUBLICATIONS

Senger et al., Science, 219, 983–985, (1983).
Folkman and Klagsbrun, Science, 235, 442–447, (1987).
Dvorak et al., J. Immunol., 122(1), 166–174, (1979).
Dvorak, N. Engl. J. Med., 315, 1650–1659, (1986).
Kadish et al., Tissue & Cell, 11, 99, (1979).
Dvorak et al., J. Natl. Cancer Inst., 62, 1459–1472, (1979).
Senger et al., Cancer Res., 46, 5629–5632, (1986).
Lobb et al., Int. J. Cancer, 36, 473–478, (1985).

*Primary Examiner*—Elizabeth C. Weimar
*Assistant Examiner*—Gail Poulos
*Attorney, Agent, or Firm*—Scott J. Meyer; James W. Williams, Jr.

[57] ABSTRACT

A method of stimulating endothelial cell growth is provided which comprises subjecting said cells to a growth stimulating amount of a highly purified vascular permeability factor having the following characteristics:

(a) it has a $M_r$ about 34,000–40,000 as determined by sodium dodecylsulfate polyacrylamide gel electrophoresis;

(b) it is a disulfide-linked protein dimer;

(c) it has a N-terminal amino acid sequence as follows:

```
 1           5              10            15
AlaProMetAlaGluGlyGluGlnLysProArgGluValValLys 16          20           25            30
PheMetAspValTyrLysArgSerTyrCysArgProIleGluMet 31       35
LeuValAspIlePheGln; and
```

(d) it exhibits substantial mitogenic activity to endothelial cells in culture.

1 Claim, 2 Drawing Sheets

STIMULATION OF ENDOTHELIAL CELL GROWTH

BACKGROUND OF THE INVENTION

This invention relates to a method of stimulating endothelial cell growth. More particularly, the invention concerns the promotion of endothelial cell growth by subjecting said cells to a growth stimulating amount of a highly purified vascular permeability factor.

Vascular permeability factors (VPFs) are proteins originally obtained from a variety of tumors which cause a rapid and reversible increase in blood vessel permeability when nanogram amounts are injected under the skin of a warm blooded mammal. VPF activity has been found in tumor ascites fluids from guinea pigs, hamsters and mice and is secreted by these tumors and a variety of tumor cell lines in vitro according to Senger et al., Science 219, 983-985 (1983).

In U.S. Pat. No. 4,456,550, a purified VPF is described which has the following characteristics:

(a) in an aqueous solution (0.01 M $Na_3PO_4$, pH 7) whose concentration of NaCl is varied linearly, VPF is eluted from a heparin-Sepharose chromatography column in a peak centered at 0.4 NaCl;

(b) in an aqueous solution of $Na_3PO_4$ (pH 7.0) whose concentration is varied linearly, VPF is eluted from a hyroxylapatite column in a peak centered at 0.25 M $Na_3PO_4$; and (c) when subjected to SDS gel electrophoresis in a 7.5% polyacrylamide slab gel (0.375 M tris-HCl, pH 8.8, 0.1% SDS) at 35 milliamps and 4° C., VPF is localized to a region corresponding to a molecular weight between 34,000 and 45,000 daltons.

The VPF was purified about 1800 fold from serum-free conditioned medium of guinea pig tumor cell culture or 10,000 fold from ascites fluid by a series of steps consisting of:

(a) affinity chromatography with a column of heparin-Sepharose;

(b) chromatography with a column of hydroxylapatite; and (c) sodium dodecylsulfate/polyacrylamide gel electrophoresis.

As little as 200 ng ($5'10^{-12}$ moles) of this purified VPF increased the vascular permeability equivalent to 1.25 $\mu g$ ($4 \times 10^{-9}$ moles) of histamine. Histamine is a standard permeability mediator described by Miles and Miles, J. Physiol. 118, 228-257 (1952). The VPF is said to have therapeutic value insofar as it enables blood nutrients to reach tissue with increased need for nutrients, as in wound healing.

According to Folkman and Klagsbrun, Science 235, 442-447 (1987), VPF causes leakage of proteins, including fibrinogen, from blood vessels, thereby initiating the formation of a fibrin gel which, in turn, may play a role in angiogenesis. See also Dvorak et al., J. Immunol. 122(1), 166-174 (1979); Dvorak, N. Engl. J. Med. 315, 1650 (1986); Kadish et al., Tissue Cell 11, 99, (1979); Dvorak et al., J. Natl. Cancer Inst. 62, 1479 (1979); and Senger et al., Cancer Res. 46, 5629-5632 (1986).

Lobb et al., Int. J. Cancer 36, 473-478 (1985), partially purified a VPF from a human adenocarcinoma cell line HT-29 having a molecular weight of 45,000. This VPF, however, does not bind to immobilized heparin as does the VPF derived from guinea pig tumor cell material by Senger and Dvorak.

BRIEF DESCRIPTION OF THE INVENTION

In accordance with the present invention a method of stimulating endothelial cell growth is provided which comprises subjecting said cells to a growth stimulating amount of a highly purified vascular permeability factor (VPF). The highly purified VPF has the following characteristics:

(a) it has a $M_r$ about 34,000-40,000 as determined by sodium dodecylsulfate polyacrylamide gel electrophoresis (SDS/PAGE);

(b) it is a disulfide-linked protein dimer;

(c) it has a N-terminal amino acid sequence as follows:

```
 1               5              10              15
AlaProMetAlaGluGlyGluGlnLysProArgGluValValLys 16              20              25              30
PheMetAspValTyrLysArgSerTyrCysArgProIleGluMet 31      35
LeuValAspIlePheGln; and
```

(d) it exhibits substantial mitogenic activity to endothelial cells in culture.

In the above amino acid sequence, conventional three letter abbreviations are used to designate the individual amino acids.

In a preferred embodiment of the invention, the foregoing highly purified VPF was isolated from serum-free conditioned culture medium of guinea pig tumor cells in a series of steps comprising:

(a) affinity chromatography of said conditioned culture medium with a column of heparin-Sepharose CL-6B;

(b) cation exchange chromatography of the VPF active fractions from said affinity chromatography with a TSK SP-5-PW column;

(c) high performance liquid chromatography (HPLC) of the VPF active fractions from said cation exchange chromatography with a Vydac $C_4$ reversed phase HPLC column; and (d) HPLC of the VPF active fractions from said $C_4$ HPLC with a Vydac $C_{18}$ reversed phase HPLC column.

The materials used in the aforesaid method of isolating the VPF are all commercially available as follows:

The heparin-Sepharose ® CL-6B is a bead formed agarose gel with heparin attached covalently which is available from Pharmacia, Inc., Piscataway, New Jersey.

The TSK SP-5-PW is a strong cation exchanger containing sulfopropyl groups bound to a silica-based support which is available from Bio-Rad Laboratories, Richmond, California.

The Vydac $C_4$ and $C_{18}$ reversed phase HPLC columns consist of $C_4$ and $C_{18}$ alkyl groups, respectively, bonded to silica supports which are available from The Separations Group, Hesperia, Calif.

Although particular methods of isolating the VPF are described herein, it will be understood that the VPF is not limited to any specific method of preparation. Thus, the VPF protein can be made by conventional recombinant DNA technology. Recent advances in biochemistry and in recombinant DNA technology have made it possible to synthesize specific proteins, for example, enzymes, under controlled conditions independent of the organism from which they are normally isolated. These biochemical synthetic methods employ enzymes and subcellular components of the protein synthesizing systems of living cells, either in vitro in cell-free systems, or in vivo in microorganisms. In either case, the principal element is provision of a deoxyribonucleic acid (DNA) of specific sequence which contains the information required to specify the desired amino acid sequence. Such a specific DNA sequence is termed a gene. The coding relationships whereby a deoxyribunucleotide sequence is used to specify the amino acid sequence of a protein is well-known and operates according to a fundamental set of principles. See, for example, Watson, *Molecular Biology of the Gene*, 3d ed., Benjamin-Cummings, Menlo Park, Calif., 1976.

A cloned gene may be used to specify the amino acid sequence of proteins synthesized by in vitro systems. RNA-directed protein synthesizing systems are well-established in the art. Double-stranded DNA can be induced to generate messenger RNA (mRNA) in vitro with subsequent high fidelity translation of the RNA sequence into protein.

It is now possible to isolate specific genes or portions thereof from higher organisms, such as man and animals, and to transfer the genes or fragments to microorganisms such as bacteria or yeasts. The transferred gene is replicated and propogated as the transformed microorganism replicates. Consequently, the transformed microorganism is endowed with the capacity to make the desired protein or gene which it encodes, for example, an enzyme, and then passes on this capability to its progeny. See, for example, Cohen and Boyer, U.S. Pat. Nos. 4,237,224 and 4,468,464.

The mitogenic activity of the VPF to endothelial cells in culture is demonstrated by an increase in cell number and in $^3$H-thymidine incorporation into deoxyribonucleic acid (DNA) relative to control cultures after several days following addition of the VPF to cultures of bovine aortic endothelial (BAE) cells. In these tests, half maximal stimulation of growth was observed at $5 \times 10^{-11}$ M VPF, and half maximal stimulation of $^3$H-thymidine incorporation into DNA was observed at $2.5 \times 10^{-12}$ M VPF. The in vitro mitogenic response, as measured by the $^3$H-thymidine incorporation, was thus about 400 times more sensitive to VPF concentration than the in vivo permeability response since the dose required for a measureable increase in permeability is $1 \times 10^{-9}$ M The mitogenic activity of VPF to endothelial cells in culture thereby is distinct and separate from its vascular permeability activity and was surprising and unexpected since the VPF did not stimulate or only slightly stimulated $^3$H-thymidine incorporation or cell growth of other cell types such as 3T3 mouse fibroblasts and mouse smooth muscle cells.

Detailed Description of the Invention

While the specification concludes with claims particularly pointing out and distinctly claiming the subject matter regarded as forming the present invention, it is believed that the invention will be better understood from the following description of preferred embodiments taken in conjunction with the accompanying drawings in which briefly:

FIG. 3 is a graphical representation which shows the $^3$H-thymidine incorporation in the embodiment of FIG. 2 in response to treatment with serum instead of VPF.

Figure 1:
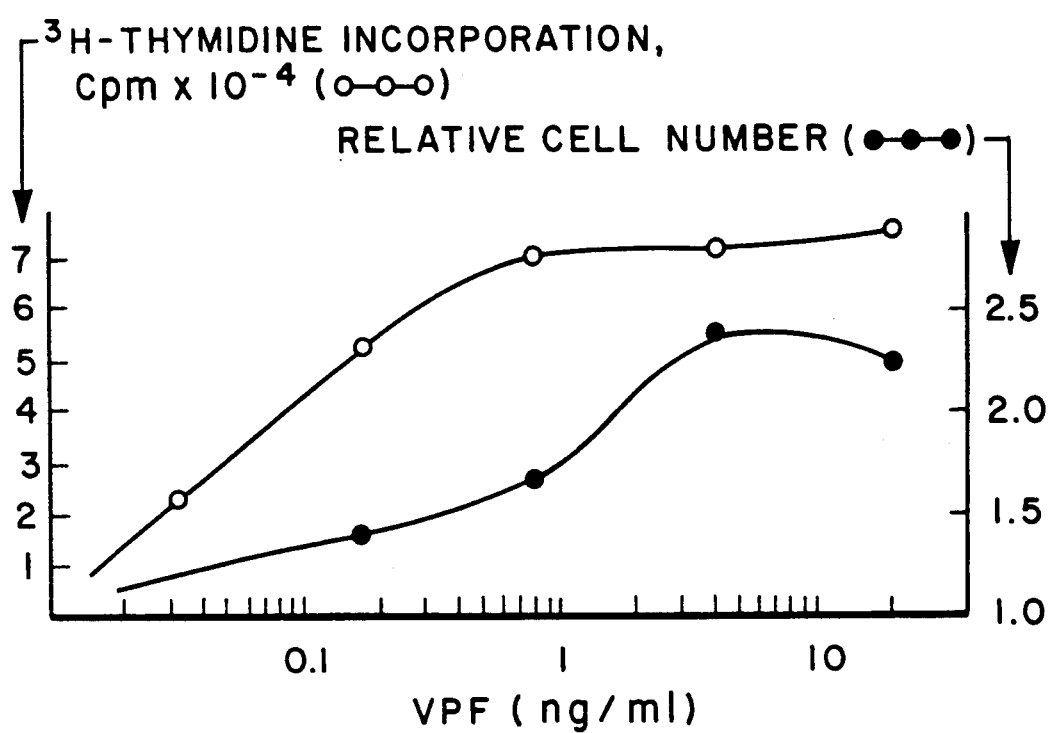
FIG. 1 is a graphical representation which shows the effect of VPF concentration on $^3$H-thymidine incorporation and growth of bovine aortic endothelial cells.

In order to illustrate the invention in greater detail, the following exemplary laboratory preparative work was carried out. In this work, Example I illustrates the production, purification and characterization of the highly purified VPF used in the method of the invention. Example II illustrates the substantial mitogenic activity of the highly purified VPF of Example I to endothelial cells in culture and comparison to other cell types.

EXAMPLE I

Materials and Methods

Growth of Guinea Pig Line 10 Cells

Guinea pig Line 10 bile duct carcinoma cells [Churchill et al., *J. Natl. Cancer Inst.* 41, 13 (1968); Rapp et al., *Ibid.* 41, 1 (1968)] were obtained from Dr. H. Dvorak and were cultured at 37° C. in Dulbecco's modified Eagle's medium (K C Biological, Inc., 4.5 g/l glucose) supplemented with 5% calf bovine serum. In T-flasks, only a small portion of the cells attached, and small clusters of cells were frequently seen. Subculture of T-flasks was performed by dividing the cultures into 4 or 5 fresh flasks. Cultures were scaled up through 500 ml, 3 L, and 12 L Bellco spinners (Bellco Glass, Inc.). Two or four 12 L spinners were used to start 100 L vibromixer reactors (Chemapec, Inc.) [Tolbert et al., *Biotech. Bioeng.* 24, 1671-1679 (1982)] with $1-2 \times 10^5$ cells/ml. A 6% $CO_2$-air blanket was kept on the cultures, and a small oxygen sparge, 2-3 cc/min, was also added via a glass sparger. Cells typically doubled in 48-72 hours, and harvests were performed once or twice a week. The harvest density typically reached $3-4 \times 10^5$ cells/ml.

The cells were aseptically harvested in a Western States solid bowl centrifuge (2100 rpm, 640 $\times$G, 2.5 L/min feed rate). The resulting cell pellet was washed in serum-free medium and repelleted (10 min, 780 $\times$G). The wash step was repeated two more times and the recovered cell volume was estimated. The cells were placed in a sterile 3 L spinner and the volume brought to 3 L. Sufficient gentamicin sulfate was then added to the spinner to achieve a concentration in the total resuspension volume (after subsequent dilution) of 25 mg/L. The spinner was allowed to mix for 15 minutes before dividing into 12 L sail spinners. [Tolbert et al., *In Vitro* 18, 311 (1982)]. The required volume of serum-free medium was added to each spinner to achieve a density of $7 \times 10^5$ cells/ml. After 24 hours, the contents of the spinners were again centrifuged, and the resulting supernatant frozen at $-20°$ C. until needed, below.

VPF Assay

The Miles permeability assay [*J. Physiol.* 118, 228-257 (1952)] was used to detect VPF. Female Hartley guinea pigs ($\sim$600 g) were shaved and the hair removed using a commercial depilating agent (Nair). Animals were anesthetized by inhalation of methoxyflurane (Metofane, Pitman-Moore, Inc.). A 1 ml volume of 0.5% (w/v) Evan's blue dye (Sigma Chemical Co.) prepared in sterile saline for injection (Abbott Laboratories) was injected intracardially into the circulation. Samples for VPF determination were prepared in saline, and 200 $\mu$l volumes injected intradermally into sites on the back of the guinea pig. The presence of VPF was indicated by an intense blue spot at the site of the injection where dye had leaked from the circulation into the tissues.

VPF Purification

Conditioned medium was filtered through a 0.45 μm Versaflow capsule (Gelman) before loading onto a 500 ml heparin-Sepharose (Pharmacia) column which had been pre-equilibrated with phosphate buffered saline (PBS). Loading was accomplished at a fast flow rate (10–20 ml/min) so that 20 L of medium could be pumped through the column in less than a day. After washing with PBS, the column was eluted at 1.8 ml/min with a linear gradient generated using 1 L each of PBS and 1.1 M NaCl in PBS. Fraction volumes of 18 ml were collected and assayed for VPF activity after diluting 1:20 with saline.

Active fractions from the above heparin-Sepharose chromatography step were pooled and extensively dialyzed against 0.01 M sodium phosphate, pH 6.1. The dialysate was centrifuged ($12,000 \times G$, 10 minutes), filtered through a 0.4 μm filter (Nalge), and applied to a $75 \times 7.5$ mm TSK SP-5-PW cation exchange column equilibrated with the same buffer. VPF was eluted with a 60-minute linear gradient of 0 to 1 M NaCl in 0.01 M sodium phosphate, pH 6.1. The flow rate was 1 ml/min. The 1 ml fractions were assayed for VPF activity after diluting 1:100 with saline.

$C_4$ and $C_{18}$ reversed phase chromatography was performed using 4.6 mm $\times$ 25 cm Vydac columns (Separations Group) containing 5 μm packing with 330 angstrom pore size. Active fractions from the above SP chromatography step were loaded directly into the $C_4$ column. The column was eluted at 1 ml/min with a gradient of acetonitrile in 0.1% trifluoroacetic acid (TFA). For $C_{18}$ chromatography, active fractions from the $C_4$ step were concentrated to about 200 μl in vacuo using a Speedvac microfuge and then diluted with an equal volume of 0.1% TFA before applying to the $C_{18}$ column. Fractions were eluted at 1 ml/min with a gradient of acetonitrile in 0.1% TFA. For assay, 10 μl aliquots were removed from each sample, diluted with 10 μl of $H_2O$ containing 10 μg bovine serum albumin (BSA), and evaporated to dryness in vacuo using a Speedvac microfuge. Saline (1 ml) was added to each sample to provide an effective 1:100 dilution prior to assay.

SDS-PAGE and NEpHGE

Analytical SDS-PAGE was performed by the method of Laemmli, *Nature* 227, 680–685 (1970), and silver staining was carried out by the method of Morrissey, *Anal. Biochem.* 117, 307–310 (1981). For preparative SDS-PAGE of active VPF, buffers were prepared with 0.1% SDS instead of 1% SDS.

Non-equilibrium pH gradient gel electrophoresis (NEpHGE) was performed under non-denaturing conditions using the following modifications of the procedure reported by O'Farrell et al., *Cell* 12, 1133–1142 (1977). Cylindrical polyacrylamide gels were cast containing 4% acrylamide, 15% (v/v) glycerol, 2.25% (w/v) ampholytes (LKB, pH 3.5–9.5) and 0.1% (w/v) Triton X-100. The acrylamide, glycerol and Triton X-100 were deionized with Bio-Rad AG 501-X8 mixed bed ion-exchange resin (equivalent amounts in $H^+$ and $OH^-$ forms) immediately prior to casting the gels. Samples containing VPF were dried in vacuo, dissolved in 0.1% (w/v) Triton X-100 and applied at the anodic end of the gel. Electrophoresis was performed at 500 V for 925 V-hours at 10.5° C. The anolyte was 0.015 M $H_3PO_4$ and the catholyte was 0.02M NaOH (degassed). Two-dimensional gel electrophoresis was performed using NEpHGE as the first dimension. The NEpHGE gels were incubated in 62.5 mM Tris-HCl, 2.3% (w/v) SDS, 5% (v/v) β-mercaptoethanol, pH 6.8, with agitation at room temperature for 10 minutes. The NEpHGE gels were then applied to polyacrylamide slab gels containing SDS for SDS-PAGE in the second dimension. Protein was detected by staining with silver.

N-Terminal Amino Acid Sequence Determination

Automated Edman degradation chemistry was used to determine the $NH_2$-terminal protein sequence of the purified VPF. An Applied Biosystems, Inc., model 470A gas phase sequencer (Foster City, Calif.) was employed for the degradations, Hunkapiller et al., *Methods. Enzymol.* 91, 399–413 (1983). The respective PTH-amino acid derivatives were identified by RP-HPLC analysis in an on-line fashion employing an Applied Biosystems, Inc., Model 120A PTH Analyzer fitted with a Brownlee 2.1 mm I.D. PTH-$C_{18}$ column. Electroblotting technology was applied to the sample in order to sequence bands isolated directly from SDS-PAGE. The methods employed were as described by Aebersold et al., *J. Biol. Chem.* 261, 4229–4238 (1986). Computer searches for comparison with known sequences were performed using a "fast p" program to probe the National Biomedical Research Foundation (Bethesda, Md.) sequence data base [updated April, 1985; Lipman and Pearson, *Science* 227, 1435–1441 (1985)], and the Genbank data base (Sequence Analysis Software Package, University of Wisconsin, Version 4.1, updated August, 1986).

Amino Acid Composition

Compositional amino acid data was collected from purified VPF samples which had been subjected to acid hydrolysis (6N HCl, evacuated sealed tubes, 24 hr., 110° C.). All analyses were performed after postcolumn derivatization of the hydrolysates using ninhydrin. A Beckman Model 6300 autoanalyzer was employed for the actual determinations.

Results

In the above four-step chromatographic method employed for the purification of VPF, conditioned medium was applied to a column of heparin-Sepharose, then eluted with a linear gradient of NaCl. VPF activity was quantitatively bound to the column, and eluted as a broad peak around 0.5 M NaCl. This step served to concentrate the activity about 50-fold from 20 L to about 400 ml, and produced about a 20-fold purification. Subsequent steps included TSK SP-5-PW cation exchange chromatography, $C_4$ RP-HPLC and $C_{18}$ RP-HPLC. A shallow gradient of acetonitrile (0.25% per minute) in 0.1% TFA was used for elution from RP-HPLC columns. The activity which eluted from the $C_{18}$ RP-HPLC column was associated with three closely-spaced $A_{215}$ absorbing protein peaks eluting at 46.9 min, 49.6 min and 52.3 min. When analyzed by SDS-PAGE and silver staining, proteins of $M_r$ 38K and $M_r$ 40K were visible. The activity corresponded closely with the elution of these proteins.

The Miles permeability assay is not suitable for precise quantitation of the amount of VPF activity in samples. However, an approximate estimate of activity can be obtained by diluting samples until a positive response is no longer obtained. By this procedure, it is estimated that the overall recovery of activity after the four purification steps was about 5-20%. About 1-2 μg of protein were obtained per liter of conditioned medium.

In the above one dimensional electrophoresis of VPF, the VPF activity corresponded closely with the presence of two $M_r$ ~40k protein bands eluting from the $C_{18}$ RP-HPLC column. These were further characterized using two dimensional gel electrophoresis, with NEpHGE as the first dimension, and SDS-PAGE as the second dimension. In one example, the sample was run under non-reducing conditions. At least six pI forms of the VPF protein were detected by this procedure. The apparent pIs were between 7 and 10. Each pI form consisted of a closely spaced molecular weight doublet in the $M_r$ 40k region.

In another example, when the VPF sample was reduced with β-mercaptoethanol prior to NEpHGE/SDS-PAGE, a similar group of proteins with pI >7 was observed. However, the molecular weights of the major bands were $M_r$ 20k and $M_r$ 24k, with a minor band observed at $M_r$ 15k. The structure of the native M ~40k protein must therefore be that of a disulfide-linked dimer. The $M_r$ 15k, 20k, 24k proteins all have similar apparent pIs.

Since the proteins detected in these preparations appeared heterogenous with respect to both charge and molecular weight, it became important to determine if any or all of observed proteins had activity. VPF was therefore subjected to either preparative SDS-PAGE or preparative NEpHGE. Gel slices were extracted with saline and assayed for activity. In the case of SDS-PAGE, the activity was found in the $M_r$ ~40k region in association with the major staining protein band. After NEpHGE, the activity also corresponded exactly with the stained proteins.

These tests confirmed that all of the observed forms in the purified preparation were indeed VPF.

Amino Acid Sequence and Composition

The N-terminal sequence for the first 36 amino acids of the intact $M_r$ ~40k VPF protein is shown in Table I. About 70-80% of the total sample contained N-terminal alanine followed by proline, as shown. Minor heterogeneity, which was believed to represent aminopeptidase degradation, was also noted. About 10-20% of the sequence contained N-terminal proline (des-ala), and about 5-10% contained N-terminal alanine followed by glutamic acid (des-ala pro met); the remainder of the internal sequence was identical to the dominant sequence. There were no potential N-linked carbohydrate sites within this sequence.

The $M_r$ 20k and $M_r$ 24k subunits were sequenced independently after reduction with β-mercaptoethanol, separation by SDS-PAGE, and electrotransfer onto derivatized GF/F paper (Table I). The sequence of the $M_r$ 20k species was identical to intact VPF for the first 15 amino acids. The $M_r$ 24k species also showed identity with the $M_r$ 40k species for amino acids 2-9; the first amino acid could not be determined unambiguously.

TABLE I

| VPF Fragment | Amino Acid Sequence |
|---|---|
| 40K | 1 5 10 15 <br> AlaProMetAlaGluGlyGluGlnLysProArgGluValValLys |
| 24K | X ProMetAlaGluGlyGluGlnLys |
| 20K | AlaProMetAlaGluGlyGluGlnLysProArgGluValValLys |
| 40K | 16 20 25 30 <br> PheMetAspValTyrLysArgSerTyrCysArgProIleGluMet |
| 40K | 31 35 <br> LeuValAspIlePheGln |

K = kilodalton

A computer search of known sequences did not reveal any significant homology VPF and previously sequenced proteins or deduced protein sequences.

The amino acid composition of intact $M_r$ 40k VPF is shown in Table II, below.

TABLE II

Amino Acid Composition of VPF

| Amino Acid | Abbrev. | Number of Residues per $M_r$ 40k VPF |
|---|---|---|
| Aspartic Acid + Asparagine | Asp + Asn | 31 |
| Threonine | Thr | 12 |
| Serine | Ser | 13 |
| Glutamic Acid + Glutamine | Glu + Gln | 77 |
| Proline | Pro | 30 |
| Glycine | Gly | 22 |
| Alanine | Ala | 11 |
| Cysteine | Cys | N.D. |
| Valine | Val | 15 |
| Methionine | Met | 1 |
| Isoleucine | Ile | 20 |
| Leucine | Leu | 18 |
| Tyrosine | Tyr | 9 |
| Phenylalanine | Phe | 15 |
| Histidine | His | 11 |
| Lysine | Lys | 38 |
| Arginine | Arg | 25 |

The amino acid composition was determined as described in Materials and Methods, above, following acid hydrolysis. Cysteine was not determined. The number of residues per $M_r$ 40k protein was calculated after averaging triplicate determinations and rounding to the nearest integer.

EXAMPLE II

Materials and Methods

Cell Growth Assays

Fetal bovine aortic endothelial cells were maintained as previously described by Olander et al., *In Vitro* 18, 99-107 (1982). Cell growth assays were conducted by plating cells in 96-well plates (600 cells per well) in 200 microliters of Dulbecco's modified Eagle's medium (DMEM) plus 10% fetal calf serum. After one day, highly purified VPF was added in fresh DMEM plus 10% calf serum. Cell number was determined after five more days using a spectrophotometric assay for acid phosphatase as described by Connolly et al., *Anal. Biochem.* 152, 136-140 (1986); U.S. application Ser. No. 736,996, filed May 22, 1985 The amount of enzyme is proportional to cell number. Control cultures usually contained about 1000 cells per well at the end of the assay period, whereas fully stimulated cultures contained up to 8000 cells per well.

3H-Thymidine Incorporation.

Cells were seeded into 24-well plates containing DMEM plus 10% fetal calf serum at a density of $1 \times 10^5$ cells/well to produce confluent monolayers. After one day, the medium was removed and replaced with serum-free DMEM, and the cells incubated an additional 24 hours. The medium was then replaced with either serum-free medium, serum-free medium plus VPF, or medium plus 10% fetal calf serum. At 18 hours, medium was replaced with 1 ml medium containing 1 $\mu$Ci (methyl-$^3$H)-thymidine (20 Ci/mmole; New England Nuclear). Plates were incubated for 2 hours at 37° C., the medium removed, then washed two times over twenty minutes with cold 10% (w/v) trichloroacetic acid (TCA) and then once with ethanol/ether (3:1, v/v). After drying at 65° C., the residue was dissolved in 0.5 ml of 0.2 M NaOH, and the radioactivity determined by liquid scintillation counting.

VPF purification and assay, and SDS-PAGE were carried out as described above in Example I. Protein concentration was determined by the method of Lowry et al., *J. Biol. Chem.* 193, 265–275 (1951), after evaporating VPF samples containing acetonitrile and TFA to dryness in vacuo using a Speedvac centrifuge.

Results

Stimulation of Cellular Growth and 3H-Thymidine Incorporation in BAE Cells by VPF.

When highly purified VPF was added to cultures of BAE cells, an increase in cell number relative to control cultures was noted after several days. FIG. 1 shows the results of a test in which increasing amounts of VPF were added to either sparse cultures of BAE cells in DMEM/10% fetal calf serum to measure the increase in cell number after 5 days, or to confluent cultures of BAE cells in serum-free DMEM to measure $^3$H-thymidine incorporation into acid-precipitable material after 1 day. It can be seen that the cell number increased 2 to 3 fold relative to controls upon exposure to 0.5–10 ng/ml VPF, and that half-maximal stimulation of growth was observed at about 2 ng/ml ($5 \times 10^{-11}$M) VPF. Increased $^3$H-thymidine incorporation by serum-deprived BAE cells into acid precipitable material occurred between 0.02 ng/ml and 1 ng/ml, with half maximal stimulation observed at about 0.01 ng/ml ($2.5 \times 10^{-12}$M) VPF.

Effect of VPF on 3H-Thymidine Incorporation by Other Cells.

Figure 2A:
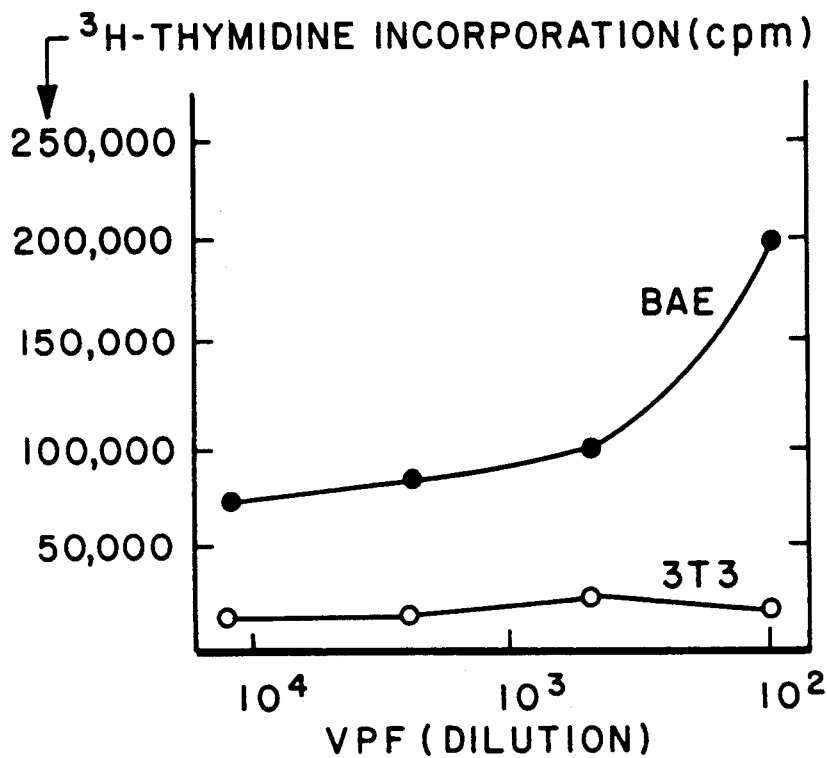
FIG. 2 is a graphical representation which shows the $^3$H-thymidine incorporation by bovine aortic endothelial cells (BAE) or 3T3 mouse cells in response to treatment with VPF.
Figure 2B:
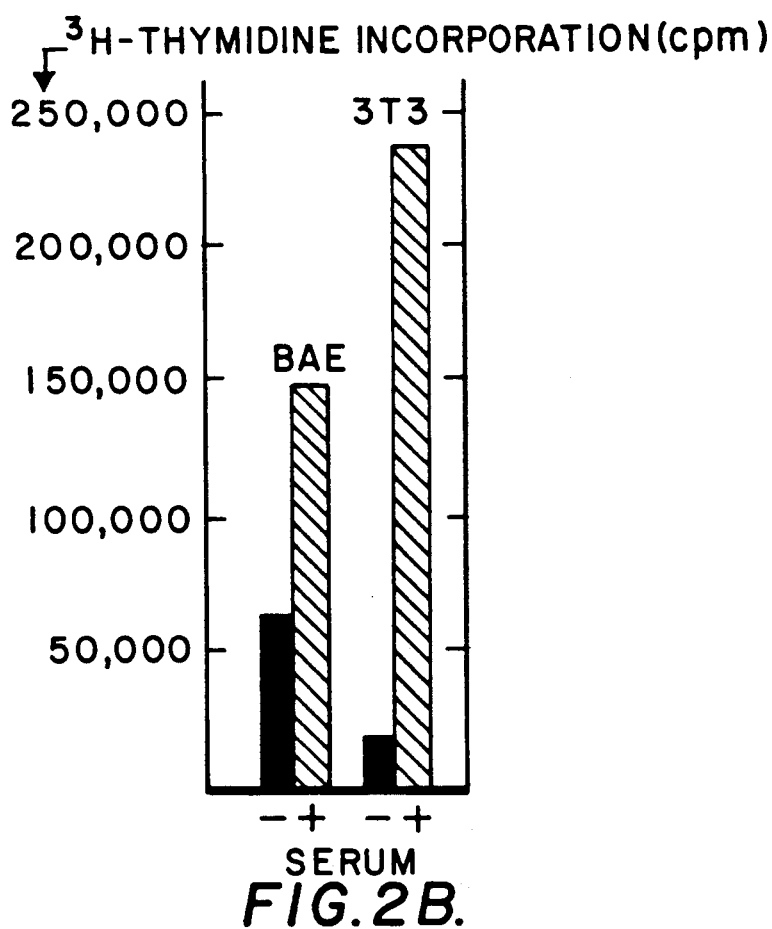

In the test shown in FIG. 2, and FIG. 3 the mitogenic response to VPF by BAE cells as measured by $^3$H-thymidine incorporation was compared with that from mouse 3T3 fibroblasts. In both cases, cells had been deprived of serum for 24 hours prior to addition of VPF. Although $^3$H-thymidine incorporation was stimulated about 3-fold in BAE cells, no increase was observed in 3T3 cells over the same concentration range of VPF. However, a mitogenic response was obtained from both cell types when serum rather than VPF was added to the serum-deprived cells. These results indicate that both cell types were capable of responding to mitogenic stimulators present in serum and that only BAE cells, but not 3T3 cells, were capable of a mitogenic response to VPF.

The affect of VPF on $^3$H-thymidine incorporation by other cell types was also examined and compared with the response to serum (Table III). In this test, all cells were deprived of serum for 24 hours, then exposed for 24 hours to either DMEM alone, DMEM containing 500 ng/ml VPF or DMEM containing 10% serum. The results show that although all of the serum-deprived cells incorporated $^3$H-thymidine in response to re-addition of serum, only BAE cells also had a significant response to VPF. The response of BAE cells to VPF was slightly greater than to serum. Although slight increases were observed for smooth muscle cells, fibroblasts, and chondrocytes, these values did not approach the levels of stimulation obtained with serum. VPF was slightly inhibitory to $^3$H-thymidine incorporation by human fetal lung fibroblasts and peripheral lymphocytes.

Molecular Weight of VPF-Associated Growth Factor Activity

Preparative SDS-PAGE of VPF-associated growth factor activity was carried out as follows: about 10 $\mu$g VPF in 0.1% TFA and 30% acetonitrile was evaporated to dryness, and dissolved in 100 $\mu$l of Laemli sample buffer [*Nature*, 227, 680–685 (1970)] with only 0.1% SDS and without $\beta$-mercaptoethanol. After electrophoresis, the gel was sliced and each fraction extracted with 1 ml saline. Each fraction was diluted an additional 100-fold and assayed for the ability to stimulate bovine aortic endothelial cell growth. It was found that all the mitogenic activity existed exclusively in the $M_r \sim 40,000$ dalton range.

TABLE III

| | | Comparison of VPF and Serum in Stimulating $^3$H-Thymidine Incorporation by Various Cell Types | | | |
|---|---|---|---|---|---|
| | | $^3$H-Thymidine Incorporation (cpm) | | | Relative Stimulation |
| Cell Type | | Serum-Free | 10% Serum | VPF (500 ng/ml) | (VPF/Serum)[1] |
| Bovine aortic endothelial | JVO17A | 78,000 | 109,000 | 115,000 | 119% |
| Bovine smooth muscle | FCSM9 | 41,000 | 159,000 | 48,000 | 6% |
| Mouse fibroblast | 3T3 | 2,000 | 81,000 | 4,000 | 2% |
| Human fetal lung fibroblast | WI38 | 40,000 | 137,000 | 27,000 | −13% |
| Bovine chondrocyte | INT | 2,000 | 55,000 | 6,000 | 8% |
| Human peripheral lymphocyte | GM892 | 42,000 | 132,000 | 19,000 | −25% |
| Mouse macrophage-line cell | WEHI-3 | 14,000 | 45,000 | 18,000 | 13% |

[1] Relative stimulation of VPF versus serum was calculated by subtracting the serum-free values from the values obtained with serum or VPF, and then determining the ratio of VPF stimulation to serum stimulation.

The highly purified VPF can be used for the stimulation of endothelial cell growth by suitable administration to a patient in need of such treatment such as, for example, as may be needed for mitogenic activity in wound healing. The amount of VPF which would normally be administered is primarily dependent upon the physical characteristics of the patient and the severity of the wound or other pathological condition. The amount must be an effective amount, that is, an amount which is medically beneficial for the growth of endothelial cells but which does not present toxic effects which overweigh the advantages which accompany its use. The preferable route of administration is parenteral, especially intradermally or subcutaneously. Administration of the VPF in solution with conventional diluents and carriers, for example, saline and albumin, is illustrative. Other suitable formulations of the active VPF in pharmaceutically acceptable diluents or carriers in therapeutic dosage can be prepared by reference to general texts in the pharmaceutical field such as, for example, *Remington's Pharmaceutical Sciences,* Ed. Arthur Osol, 16th ed., 1980, Mack Publishing Co., Eastman, Pa.

Various other examples will be apparent to the person skilled in the art after reading the present disclosure without departing from the spirit and scope of the invention. It is intended that all such other examples be included within the scope of the appended claims.

What is claimed is:

1. The method of stimulating endothelial cell growth in vitro comprising subjecting said cells to a growth stimulating amount of a highly purified vascular permeability factor having the following characteristics of guinea pig VPF:

(a) it has a $M_r$ about 34,000–40,000 as determined by sodium dodecylsulfate polyacrylamide gel electrophoresis;

(b) it is a disulfide-linked protein dimer;

(c) it has a N-terminal amino acid sequence as follows:

```
1          5              10             15
AlaProMetAlaGluGlyGluGlnLysProArgGluValValLys 16         20             25             30
PheMetAspValTyrLysArgSerTyrCysArgProIleGluMet 31         35
LeuValAspIlePheGln; and
```

(d) it exhibits substantial mitogenic activity to endothelial cells in culture.

* * * * *